US010215673B2

(12) United States Patent
Schryver et al.

(10) Patent No.: US 10,215,673 B2
(45) Date of Patent: *Feb. 26, 2019

(54) VENTILATION ASSISTED PASSIVE CELL FREEZING DEVICE

(71) Applicant: Cool Lab, LLC, Chelmsford, MA (US)

(72) Inventors: Brian Schryver, Redwood City, CA (US); Scott Ganaja, San Luis Obispo, CA (US)

(73) Assignee: Cool Lab, LLC, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,544

(22) Filed: Jan. 3, 2017

(65) Prior Publication Data
US 2017/0184479 A1 Jun. 29, 2017

Related U.S. Application Data

(63) Continuation of application No. 14/118,542, filed as application No. PCT/US2012/038431 on May 17, 2012, now Pat. No. 9,534,992.

(60) Provisional application No. 61/487,445, filed on May 18, 2011.

(51) Int. Cl.
*G01N 1/42* (2006.01)
*A01N 1/02* (2006.01)

(52) U.S. Cl.
CPC ............ *G01N 1/42* (2013.01); *A01N 1/0252* (2013.01)

(58) Field of Classification Search
None
See application file for complete search history.

(56) References Cited

U.S. PATENT DOCUMENTS

| | | |
|---|---|---|
| 4,030,314 A | 6/1977 | Strehler |
| 4,107,937 A | 8/1978 | Chmiel |
| 4,455,842 A | 6/1984 | Granlund |
| 4,530,816 A | 7/1985 | Douglas-Hamilton |
| 4,807,442 A | 2/1989 | Linner |
| 5,726,360 A | 3/1998 | Keefer |
| 6,347,525 B2 | 2/2002 | Cosman |
| 6,381,967 B1 | 5/2002 | Craig |
| 6,393,860 B1 | 5/2002 | Heschel |
| 6,718,775 B2 | 4/2004 | Colombo |
| 8,318,499 B2 | 11/2012 | Fritchie |
| 2009/0019865 A1* | 1/2009 | Henderson ............... A01N 1/00 62/62 |
| 2009/0133411 A1* | 5/2009 | Cheng ................. A01N 1/0252 62/62 |
| 2009/0173472 A1 | 7/2009 | Schryver |
| 2010/0112261 A1* | 5/2010 | Van Lumig ............. B32B 1/08 428/36.91 |
| 2014/0083212 A1 | 3/2014 | Schryver |

FOREIGN PATENT DOCUMENTS

| | | |
|---|---|---|
| WO | WO 91/02200 | 2/1991 |
| WO | WO 2009/062025 | 5/2009 |

\* cited by examiner

*Primary Examiner* — Paul West
*Assistant Examiner* — Mark A Shabman
(74) *Attorney, Agent, or Firm* — Kirton & McConkie; David Conklin

(57) ABSTRACT

A system and method for concurrently and uniformly removing thermal energy from clustered specimen samples.

20 Claims, 7 Drawing Sheets

VENTILATION ASSISTED PASSIVE CELL FREEZING DEVICE

This application is a Continuation of U.S. patent application Ser. No. 14/118,542, filed Nov. 18, 2013, entitled VENTILATION ASSISTED PASSIVE CELL FREEZING DEVICE, which is a National Stage of International Application No. PCT/US2012/038431, filed May 17, 2012, and entitled VENTILATION ASSISTED PASSIVE CELL FREEZING DEVICE, which claims the benefit of U.S. Provisional Application No. 61/487,445, filed May 18, 2011, and entitled VENTILATION ASSISTED PASSIVE CELL FREEZING DEVICE. This application claims priority to and incorporates herein by reference the above-referenced applications in their entirety.

BACKGROUND OF THE INVENTION

Maximizing the percentage of suspended cells recovered live following freezing, archival storage, and thawing requires that a specific temperature reduction profile be applied (see U.S. Patent Application Pub. No. 2011/0308271 and PCT Pub. No. 2011/159934, each of which is incorporated herein by reference). When freezing multiple vials concurrently, it is therefore critical that each vial experience the same desired profile. While passive cell freezing systems offer a significant cost savings over actively managed temperature reduction systems, current passive freezing system designs that offer vial freezing rate uniformity depend upon a circular array of the vials to produce uniform thermal energy release to the surrounding environment. The need for a circular array places a practical limit on the number of vials that can be contained in a freezing unit, as the circumference of the device increases in a linear proportion to the number of vials contained therein.

The sample vials may be confined in a densely packed array; however, this arrangement will require that, for a portion of the vials, the path of heat transfer will at least partially be directed through or past adjacent vials, thereby imposing a variable thermal gradient environment for the vial collection during the freezing process. This condition will inevitably result in a spectrum of temperature reduction profiles, only a fraction of which may be appropriate for optimal cell viability upon thawing. In addition, as the number of vials in the cluster is increased, so will the thermal mass of the collection. To maintain the desired temperature reduction profile, a greater quantity of thermal energy will need to be released per unit time, thereby necessitating a reduction in the thickness of the insulation of the passive cooling device, thereby imposing an even greater imbalance in the freezing rates between the exterior and interior vials of the cluster.

As the sample capacity of the freezing device is increased, a secondary problem arises in that, upon completion of the freezing process, the samples will need to be transferred to archival storage. Transferring the vials individually is both time consuming and presents opportunity for frozen specimens to warm, thereby presenting a great threat to the integrity and viability of the frozen cells.

Thus, there remains a need for passive cooling/freezing devices to achieve the desired temperature reduction profile for clustered sample vials. The present invention meets this need.

SUMMARY OF THE INVENTION

The present invention provides an insulating chamber that surrounds a cluster of sample vials and their contents. In some embodiments, the chamber is constructed from an insulating material such as polyethylene, styrene, or urethane foam. The insulating chamber further comprises a gas inlet port and a gas outlet port, wherein the gas inlet port is located at or near an underside of the chamber, and wherein the gas outlet port is located at or near a top side of the chamber. The gas ports may further be configured to receive restrictors or baffles for the purpose of regulating the flow of gases through the gas ports. In some embodiments, the restrictors contain a single hole or port; in other embodiments, the restrictors contain a plurality of holes or ports. The cross-sectional shape and size of the gas ports may further be adjusted to provide a desired amount of gas flow or fluid dynamic. In other embodiments the gas ports may comprise one or more valves for the purpose of regulating gas flow into and out of the chamber. In some embodiments, valves are provided which may be manually adjustable for the purpose of gas flow regulation. The chamber may further comprise two or more interlocking sections to facilitate placement and removal of sample vials within the chamber.

In some embodiments, the cluster of sample vials within the chamber is contained or stored within a removable rack. When inserted within the chamber, the removable rack acts to divide the interior of the chamber into an upper and lower chamber. In many embodiments, the rack rests directly upon an interior, annular rim protrusion which forms a portion of an interior wall surface of the chamber. The rim protrusion may be positioned such that the interior of the chamber is divided into upper and lower chambers by the rim. The upper and lower chambers may be further spatially defined by placement of the removable rack onto the rim protrusion, wherein the removable rack provides a physical barrier between the two chambers.

Various embodiments of the present invention provide a gaseous pathway through the interior of the chamber and the removable rack. For example, a gas (typically air) may enter the lower chamber via the one or more ports and pass into the upper chamber via gas vents provided in the removable rack. The lower chamber is further configured such that a gas enters the lower chamber via the inlet port and flows through the gas vents of the removable rack and into the upper chamber.

Gas flow through the insulating chamber is facilitated by thermodynamic principles. For example, when the device is placed in a freezer, cold gas introduced into the lower chamber via the inlet port forces warm gas from the lower chamber, through the removable rack and into the upper chamber. Excess cold gas within the lower chamber is forced though the removable rack and into the upper chamber, thereby forcing warm gas within the upper chamber to exit the insulating chamber through the outlet port. Heat is removed from the vial samples by the cold gas, thereby warming the gas surrounding the sample vials. The warmed gas is less dense than the cold gas, so the cold gas entry causes the warmed gas to move upwardly into the upper chamber and exit the device via the outlet port. As the warmed gas exits the upper chamber, additional cold gas is drawn into the lower chamber via the inlet port. The introduction of cold gas into the lower chamber forces warmer gas within the lower chamber to pass through the removable rack and into the upper chamber, thereby continuing the cooling process. The exchange of gases within the upper and lower chamber ceases once temperature equilibrium is reached between the lower chamber, the upper chamber, the vial samples, and the exterior environment.

In some embodiments, the outlet port comprises a one-way port, such that gas is prevented from entering the upper chamber via the outlet port. Rather, gas is permitted to enter the upper chamber solely by passing through the gas vents from the lower chamber. Further, in some instances the input port comprises a one-way port, such that gas is prevented from exiting the lower chamber via the input port. Rather, gas within the lower chamber must exit the device through the outlet port after passing through the gas vents of the removable rack and the upper chamber.

In some embodiments, the sample vial rack comprises a plurality of wells or openings for the purpose of receiving one or more sample vial tubes. In other embodiments, the rack forms an airtight seal with the rim such that gas must pass through the gas vents of the removable rack to move between the upper and lower chambers. For example, the removable rack in some embodiments comprises a continuous surface having a size and shape compatible interface with the rim protrusion around the perimeter of the chamber. The wells or opening are configured in some embodiments to maximize or minimize contact with the sample vial. For example, in some embodiments the removable rack comprises a thermoconductive material, such that the temperature of the vial sample is in part regulated by the temperature of the removable rack. In these embodiments, one can maximize surface contact between the vial sample and the opening or well of the rack. In other instances, the removable rack comprises a thermally inert material, such that the temperature of the vial sample is regulated primarily by contact with the gas within the insulating chamber. Accordingly, in these latter embodiments, one can limit contact between the removable rack and the sample vial, and so maximize exposure of the vial sample to the gas within the insulating chamber. The rack may further comprise one or more holes positioned between selected vials for the purpose of directing gas flow around the sample vials, or directly into contact with the sample vials. In various embodiments, the rack is composed of polypropylene or polyethylene or plastic blends of those two polymers as the main or only components.

In some embodiments, the sample rack and sample vial payload may be transferred as a single unit to an archival storage site, such as a sample freezer. As such, some systems of the present invention eliminate the need to transfer sample vials to an archival storage site individually.

In some embodiments, the sample vials are introduced into the removable rack after the removable rack is seated within the insulating chamber on the rim protrusion. In other instances, the sample vials are first loaded into the removable rack and then introduced into the insulating chamber by placing the removable rack into the insulating chamber. The insulating chamber includes a base and lid or cover, wherein upon placing the cover over the base (in some embodiments, the cover and base are configured to interlock when closed), the removable rack is enclosed within the insulating chamber, which then can be placed into an environment of reduced temperature. As the environmental gases in the reduced temperature environment will be of greater density than the warmer gases contained within the interior of the insulating chamber, colder gases will enter through the underside vent and displace the gases of greater temperature and lesser density which will in turn exit through the top vent. As the cold gases contact the warmer sample vials, thermal energy will be transferred to the gases from the vials. Upon gaining thermal energy, the gases will be reduced in density and become displaced by a continuous influx of colder gas. As such, by selective placement of gas passage holes in the rack surface, thermal energy may be removed from specific vials in the central portion of the vial cluster, thereby equalizing the rate of thermal energy loss from all vials contained within the chamber of the invention. The overall rate of thermal energy loss, and therefore the rate of sample vial temperature reduction, can be adjusted by various combinations of vent restriction, rack gas passage hole size and placement, and chamber insulation thickness.

DETAILED DESCRIPTION OF THE INVENTION

The present invention will be described with regard to the accompanying drawings, which assist in illustrating various features of the invention.

Figure 1:
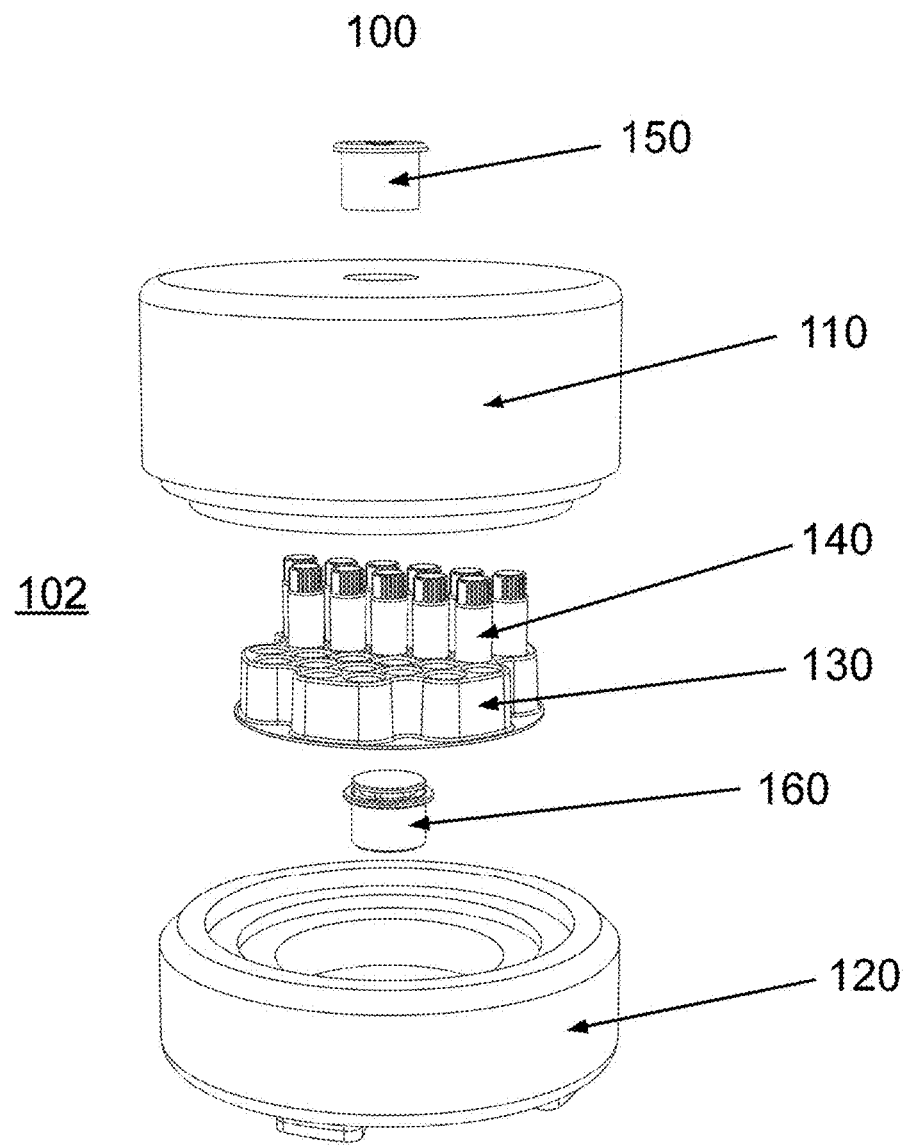
FIG. 1 is an exploded view of a sample freezing apparatus and removable rack in accordance with a representative embodiment of the present invention.

Referring now to FIG. 1, a sample freezing apparatus 100 is shown. Sample freezing apparatus 100 generally comprises an enclosure having an internal, insulating chamber in which a removable rack 130 is placed and enclosed. The insulating chamber of sample freezing apparatus 100 generally comprises a thermo-insulating material, such as polyethylene, polystyrene, or polyurethane foam materials. The insulating chamber may further include additional materials to enhance or otherwise optimize the insulating needs of the device. For example, apparatus 100 may comprise additional internal or external insulating material to provide additional insulation. Alternatively, apparatus 100 may comprise one or more compartments or lines for the addition of a cooling agent, such as liquid nitrogen or a pre-cooled ballast mass.

In some embodiments, sample freezing apparatus 100 comprises a base 120 having a top end comprising an opening having a perimeter surface for compatibly receiving a lid or cover 110. Lid 110 generally comprises a bottom end having an opening comprising a perimeter surface for compatibly interconnecting with the top end of base 120. Base 120 and lid 110 are thus configured to interconnect compatibly, thereby isolating the internal, insulating chamber from an exterior environment 102 surrounding the apparatus 100. Base 120 may further comprise one or more legs or supports, whereby to provide clearance between a bottom surface of base 120 and a surface on which base 120 is supported.

Base 120 further comprises an internal surface for receiving and supporting removable rack 130. In some instances, base 120 comprises an inner wall surface having an annular rim protrusion or shelf that provides a surface on which an outer circumferential portion of removable rack 130 is seated. Thus seated, removable rack 130 divides and spatially separates an interior volume of base 120 from an interior volume of lid 110. In some instances, removable rack 130 divides the internal, insulating chamber of apparatus 100 into an upper chamber and a lower chamber, wherein the upper chamber corresponds to the interior volume of lid 110 and the lower chamber corresponds to the interior volume of base 120.

Base 120 can comprise an inlet valve or port 160 that is inserted into an opening within a bottom end or portion of base 120. Inlet port 160 provides gaseous communication between the lower chamber and the exterior environment surrounding apparatus 100. In some embodiments, inlet port 160 comprises a one-way port, thereby preventing gas within the lower chamber from exiting the lower chamber via inlet port 160. Gas or air from the exterior environment enters the lower chamber via inlet port 160.

Similarly, lid 110 can comprise an outlet valve or port 150 that is inserted into an opening within a top portion or top surface of lid 110. Outlet port 150 provides gaseous communication between the upper chamber and the exterior environment. In some embodiments, outlet port 150 comprises a one-way port, thereby preventing gas from the exterior environment from entering into the upper chamber via outlet port 150. Gas within the upper chamber exits the upper chamber via outlet port 150.

Removable rack 130 can comprise any shape, size, and configuration desired to seat compatibly within device 100 when lid 110 is coupled to base 120. In some instances, removable rack 130 comprises a perimeter edge that is configured to seat within base 120 on a ledge, shelf, or other annular rim protrusion of base 120. The interface between removable rack 130 and base 120 provides a tight seal thereby preventing or materially restricting passage of gas (typically air) between the upper chamber and the lower chamber. In some instances, removable rack 130 comprises one or more holes or gas vents that gaseous communication between the upper and lower chambers. Thus, gas within the lower chamber may flow through removable rack 130 via the one or more gas vents and into the upper chamber. Similarly, gas within the upper chamber may flow through removable rack 130 via the one or more gas vents and into the lower chamber.

In some embodiments, a plurality of sample vials 140 is held or secured within wells or openings of removable rack 130. In some instances, sample vials 140 are placed into removable rack 130 prior to placing removable rack 130 within base 120. In other instances, removable rack 130 is first placed into base 120 and subsequently loaded with sample vials 140. Once loaded, base 120 is interlocked with lid 110 thereby confining removable rack and sample vials within the insulating chamber.

Removable rack 130 may comprise any material or combination of materials compatible with the teachings of the present invention. For example, in some embodiments removable rack 130 comprises a thermoconductive material, such as aluminum, copper, silver, gold, zinc, steel, and/or alloys thereof. In other embodiments, removable rack 130 comprises a thermally inert material, such as a weatherable polymer material. For example, removable rack 130 is in various embodiments composed of polypropylene, polycarbonate, polyvinyl chloride, or polyethylene polymers. Further, in some embodiments, removable rack 130 comprises a combination or thermoconductive and thermally inert materials, wherein the thermoconductive materials are in direct contact with the sample vials. As such, heat is transferred from gases within the insulating chamber to the sample vials via the thermoconductive material.

Figure 2:
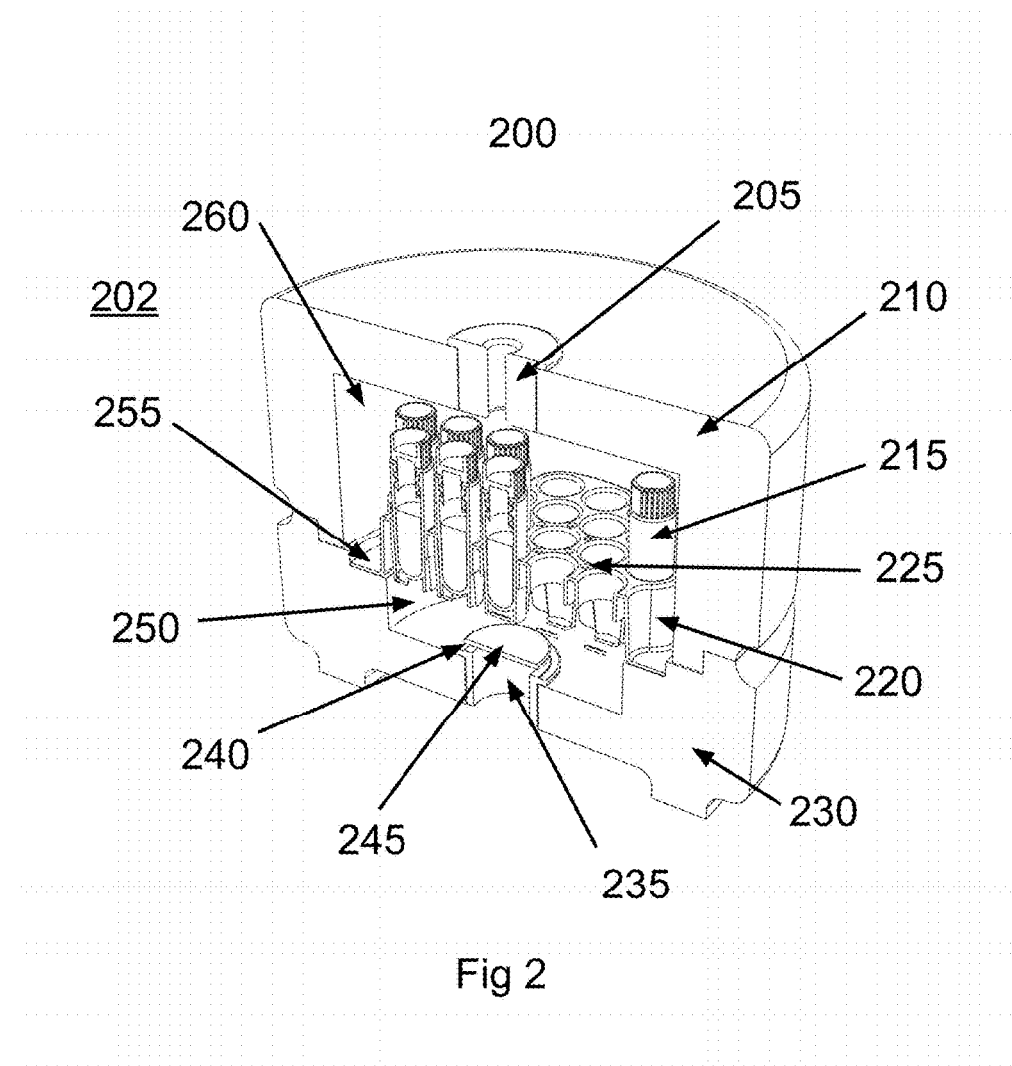
FIG. 2 is a cross section perspective view of an assembled sample freezing apparatus and removable rack in accordance with a representative embodiment of the present invention.

Referring to FIG. 2, an assembled sample freezing apparatus 200 of the present invention is shown in cross section. In some embodiments, an insulating base 230 supports a removable rack 220 such that the insulating chamber is divided into an upper chamber 260 and a lower chamber 250. Further, the placement of removable rack 220 suspends sample vials 215 between upper and lower chambers 250 and 260. The insulating base 230 further contains a portal opening into which an input port 235 is inserted. Insulating base 230 may include one or more input ports as may be desired. Input port 235 provides gaseous communication between lower chamber 250 and external environment 202. When placed from a warm environment into a colder environment, denser gases from the surrounding cold environment enter input port 235 into lower chamber 250. Warmer and less dense gas contained in lower chamber 250 is displaced from lower chamber 250 by the denser, cold gas from the colder environment. As a result, warm air within lower chamber 250 is forced into upper chamber 260 via gas vents 225 in removable rack 220. As warm air from lower chamber 250 enters upper chamber 260, warm air within upper chamber 260 is displaced from upper chamber 260 via outlet port 205.

In some embodiments, a vacuum is created within upper and lower chambers 260 and 250 as gas leaves upper chamber 260 via output port 205. This vacuum pressure draws additional cold gas into lower chamber 250 via input port 235. In other embodiments, the higher density of the cold air forces the lower density warm air from the lower chamber 250 into the upper chamber 260, and subsequently from the upper chamber 260 to external environment 202 via output port 205. As cold gas replaces warmer gas within the upper and lower chambers, heat is removed from sample vials 215 thereby warming the gas within the chambers. This warm gas is subsequently replaced by additional cold gas that enters lower chamber 250 via input port 235. The flow of gas through lower and upper chambers 250 and 260 ceases or slows as the temperatures of the gases in the upper and lower chambers, the sample vials, and removable rack 220 reach equilibrium with the exterior environment.

In some embodiments, input vent 235 further comprises a blind terminus cap 245 or deflector cap that causes gases entering lower chamber 250 to deflect laterally through vent ports 240 to fill lower chamber 250 uniformly. Removable rack 220 may further include a plurality of gaps located between the sample vials 215 and the removable rack 220. These gaps permit cold gases to pass through removable rack 220 from lower chamber 250 and into upper chamber 260. Gas pathway flow may also be directed through a plurality of gas vents 225 in the removable rack for the purpose of adjusting the temperature change rate of specific sample vials. The size, cross-sectional shape, and placement of gas vents 225 can be selected to increase or decrease contact between the gases moving through vents 225 and sample vials 215 stored in removable rack 220. For example, in some embodiments, gas vents 225 are placed around the perimeter of each sample vial, thereby promoting contact between the migrating gases and the sample vials 215. In other embodiments, gas vents 225 are angled such that gases are directed towards sample vials 215 as the gases exit the vents into the upper chamber 260.

During the passage of cold gases over the sample vials, thermal energy is transferred to the cold gas from the warmer vial surface. This transfer of heat cools the vial sample and increases the temperature of the gases passing over the sample vials. The densities of these gases are reduced thereby further facilitating movement of the gases through the upper chamber 260 and outlet port 205. This process creates a continuous flow of cold gas over the vials until the temperature of the vials is equal to that of the environment.

Figure 3:
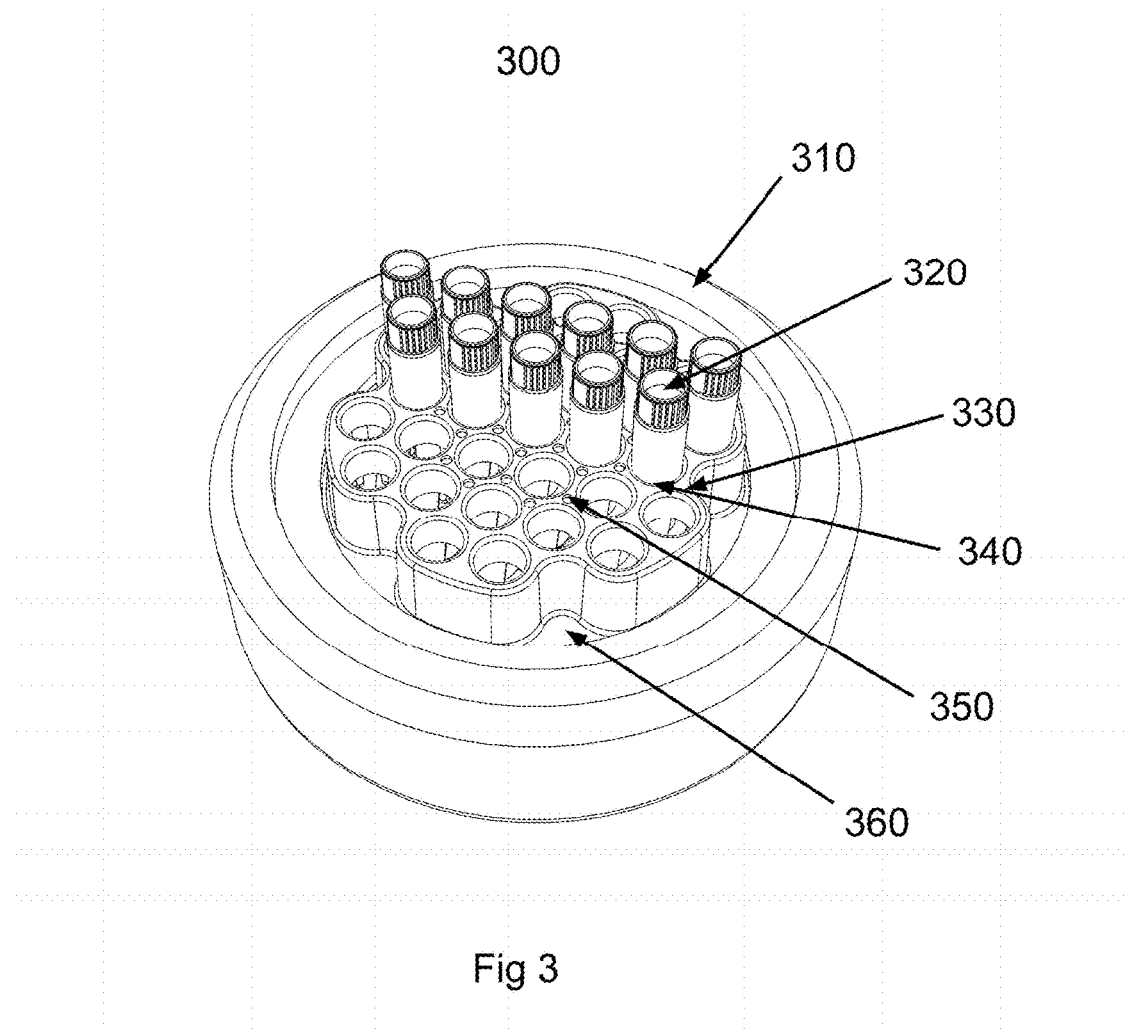
FIG. 3 is a top view of the base of a sample freezing apparatus, a removable rack, and sample vials in accordance with a representative embodiment of the present invention.

Referring to FIG. 3, a view 300 of the insulating base 310, removable rack 330 and sample vials 320 is shown. In some embodiments, gas flow through the removable rack is blocked at various positions where the removable rack 330 forms an interface with insulating base 310. For example, removable rack 330 may comprise one or more baffle extensions 360. Baffle extension 360 may comprise a webbing of removable rack 330, which provides removable rack 330 with a circumferential perimeter that compatibly seats within base 310. Thus, baffle extensions 360 form a seal between removable rack 330 and base 310. This seal further forces gases within the lower chamber to pass into the upper chamber vial gas vents 350. In other embodiments, gases are directed past the sample vials through the gap 340 between the removable rack 330 and the sample vials 320.

Figure 4:
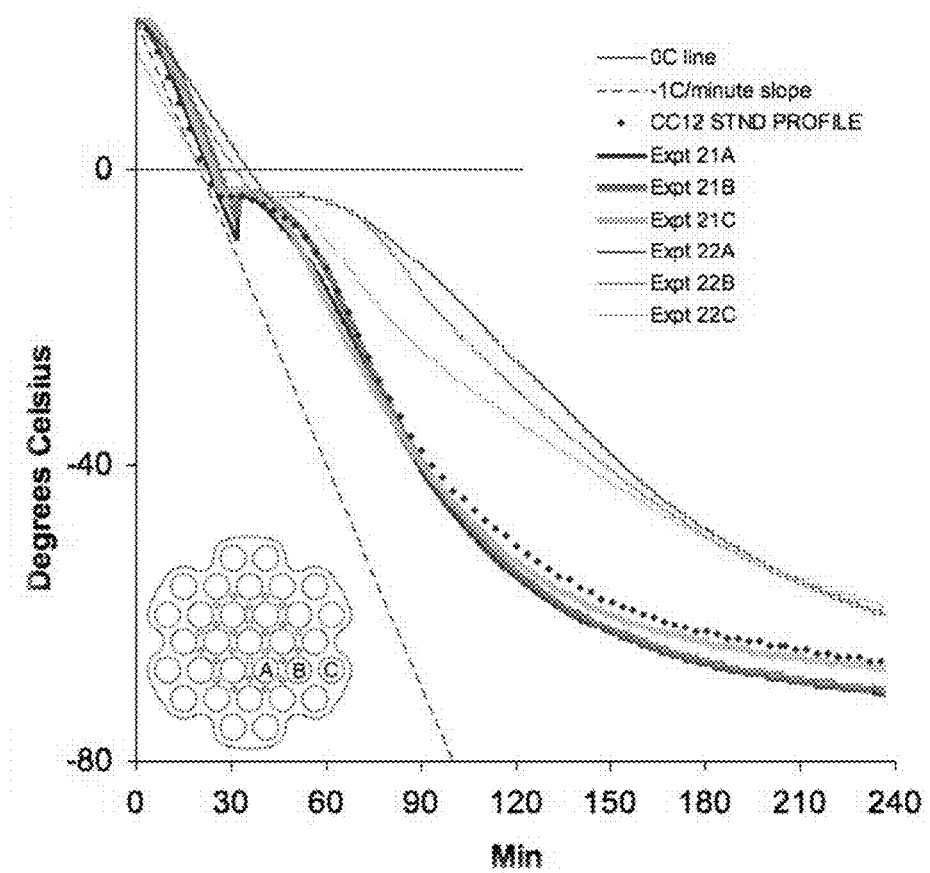
FIG. 4 is a graphic representation of the freezing rates of three vials representing three concentric distances from the vial cluster center, demonstrating the ability of air flow compensation both to accelerate the overall freezing rate and to equalize the freezing rates within the vial cluster, in accordance with a representative embodiment of the present invention.

Referring to FIG. 4, results from an experiment are shown, wherein data was derived from three representative vials placed at positions representing three concentric distances from the center of a removable rack. The specific vial positions are shown in the drawing inset for vials "A", "B", and "C". The target cooling rate slope of 1 degree Celsius per minute is represented by the dashed line and depicts the freezing rate profile ("CC12") obtained using the Biocision (Larkspur, Calif.) CoolCell∩ freezing device, wherein the sample rack was loaded with 12 samples to provide the standard target curve. Three solid traces represent the freezing profiles obtained from sample vials A, B, and C, with a 25 degree Celsius starting temperature when a device of the invention is placed into a −75 degree Celsius environment with the underside and top vents completely blocked to gas flow.

As shown by the graph, the outermost vial C experiences the fastest freezing rate, while the middle vial B experiences an intermediate freezing rate, and the innermost vial A experiences the slowest freezing rate. All freezing rates obtained under these conditions are slower than the desired profile provided by the CC12. When the freezing process is repeated with unblocked vents, the same vials report the additional traces shown. The close proximity of the additional traces to the desired freezing profile shown demonstrates the ability of the vented device to equalize the freezing rates within a vial cluster.

Figure 5:
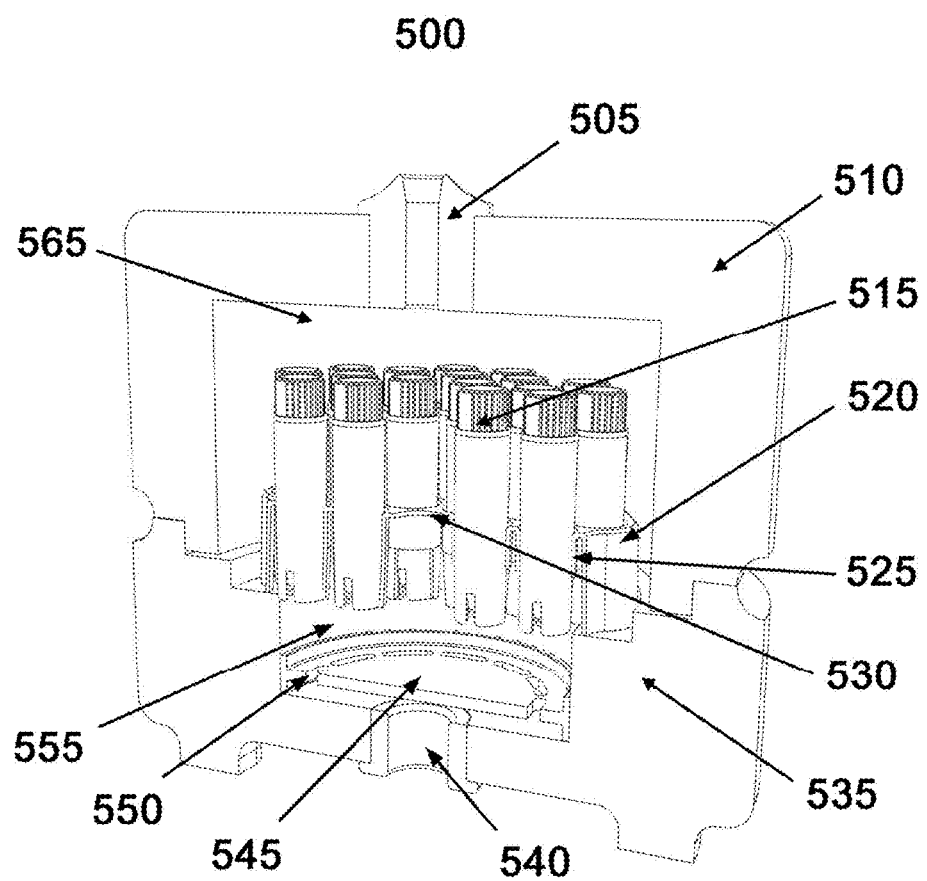
FIG. 5 is a cross section perspective view of an assembled sample freezing apparatus and removable rack with sample vials in accordance with a representative embodiment of the present invention.

Referring to FIG. 5, a sample freezing apparatus 500 of the invention is shown fully assembled and in cross section. In some embodiments, an insulating base 535 supports a removable rack 520 such that sample vials 515 are suspended between upper and lower chambers 565 and 555, respectively. Removable rack 520 is further positioned such that upper chamber 565 is separated from lower chamber 555 by an interface between removable rack 520 and insulating base 535. As with the previous embodiments, insulating base 535 comprises a portal opening into which an inlet port 540 is inserted. When placed from a warm environment into a colder environment, the denser gases from the surrounding cold environment enter the inlet port 540 thereby displacing the warmer and less dense gas contained in the lower chamber 555 and the upper chamber 565. Warmer and less dense gases within the lower and upper chambers exit the upper chamber 565 through outlet port 505.

In some embodiments, gases entering inlet port 540 are deflected laterally by a deflector plate 545. Deflector plate 545 may include any size, shape, and/or configuration to achieve a desired distribution of cold gases into lower chamber 555. For example, in some embodiments, deflector plate 545 comprises a disc having a plurality of slots or openings positioned around the perimeter of the disc. In some embodiments, the slots or openings of deflector plate 545 are not aligned with gas vents or gaps of removable rack 520. Further, in some instances deflector plate 545 comprises a removable component that may be selectively inserted within an internal cavity or space of insulating base 535. In some instances a removable rack and a removable deflector plate are provided as a matched pair for use in combination to achieve a desired rate of cooling.

In some embodiments, gas pathway flow from lower chamber 555 is directed through a central hole 530 in removable rack 520 thereby increasing the gas flow rate for the central vials. The diameter of central hole 530 can be selected to optimize and/or equalize the rate of heat transfer from the vials. Upper vent 505 can have a conical exterior profile, as shown. This profile is useful to prevent accidental blockage of the port, such as by the placement of objects on the top of the assembly 500 during the freezing process. Unless the blocking object is purposely balanced on the exit opening of the vent 505, the object will tip to one side and unblock the vent opening.

Figure 6:
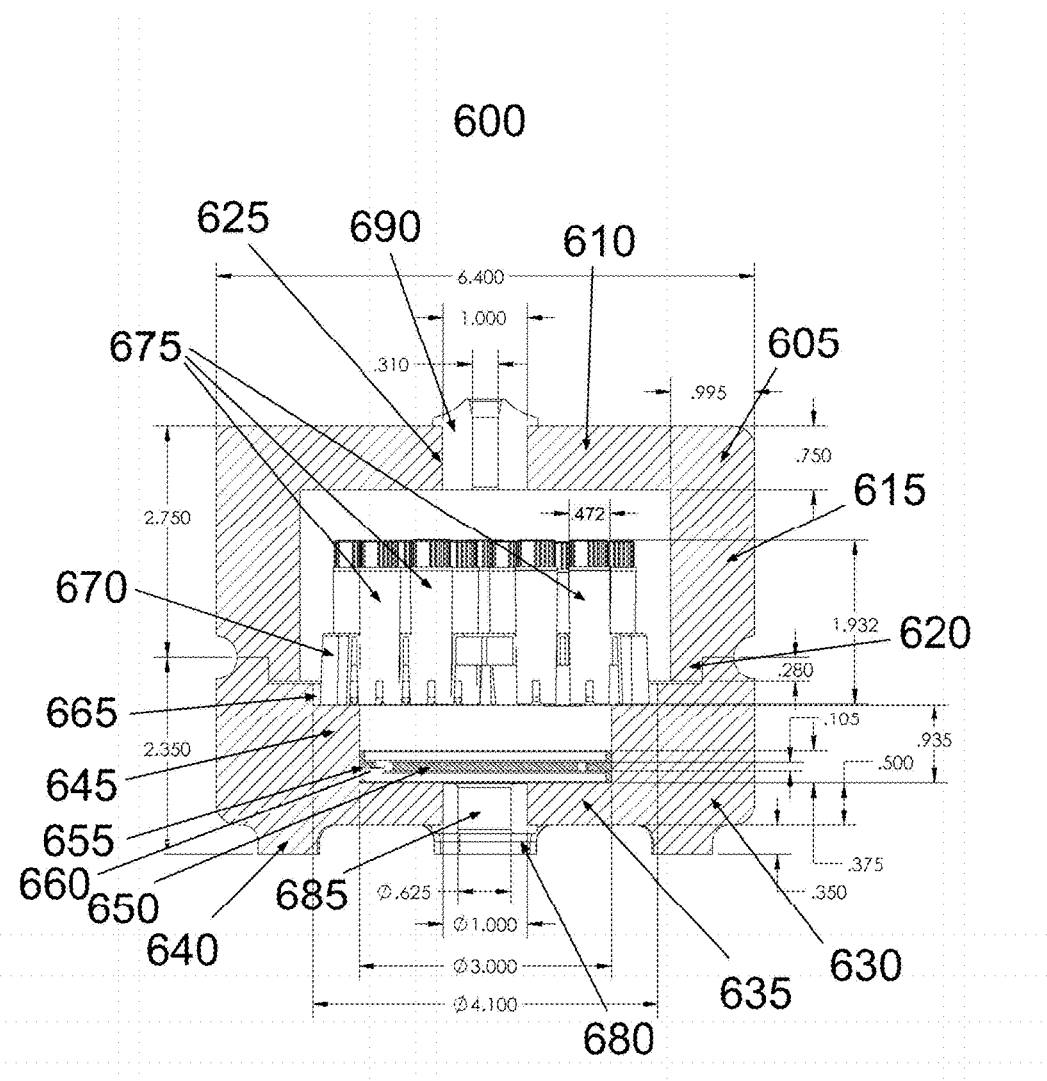
FIG. 6 is a dimensioned front cross section perspective view of an assembled sample freezing apparatus and removable rack with sample vials in accordance with a representative embodiment of the present invention.

Referring to FIG. 6, a sample freezing apparatus 600 of the invention is shown in frontal cross section with dimensions for specific features provided. In some embodiments, the upper cover 605 is a cylindrical shell constructed from high density polyethylene foam with an outside diameter of approximately 6.4 inches and a height of approximately 2.750 inches. The upper cover further comprises a flat top 610 with a thickness of approximately 0.75 inches. The cylindrical walls of cover 615 have a thickness of approximately 0.995 inches. In some embodiments, the cylindrical wall of the cover terminates on the lower side in a ring projection 620 that interlocks by friction fit to an annular ring projection or protrusion on lower base 630.

Upper cover 605 further comprises a central hole 625 with a diameter of approximately one inch that is sized and configured to receive a top vent choke 690. Top vent choke 690 is constructed from a weatherable polymer material and includes a cylindrical central passageway having a diameter of approximately 0.31 inches. Lower base 630 is constructed from the same high density polyethylene foam as the upper cover 605 and has a cylindrical shape with the same outside diameter as upper cover 605. In some embodiments, lower base 630 comprise an overall height of approximately 2.350 inches.

In some embodiments, the base floor of the cylinder 635 has a thickness of approximately 0.5 inches and is supported by four foot extensions 640 which have a height of approximately 0.35 inches. Lower base 630 further comprises a cylindrical interior shelf 645 that supports the removable sample tube rack 670.

Removable sample tube rack 670 is supported by interior shelf 645 and restricted in lateral movement by an interior surface 665 of lower base 630, wherein the interior surface 665 has a diameter of approximately 4.1 inches. Lower base 630 further comprises a vertical cylindrical surface of interior shelf 645 which comprises a diameter of approximately 3 inches and is configured to receive and house an alloy diffusion plate 650. In some embodiments, alloy diffusion plate 650 comprises a thickness of approximately 0.105 inches. Alloy diffusion plate 650 further comprises an annular array of slots 660 through which gases are permitted to pass. Alloy diffusion plate 650 is supported by a cylindrical flange 655 of lower base 650, wherein cylindrical flange 655 comprise a height of approximately 0.375 inches and serves to form a gas seal with the vertical cylindrical surface of shelf 645.

In some embodiments, removable sample tube rack 670 is configured to hold 30 sample tubes 675, wherein each sample tube 675 comprises an average diameter of approximately 0.472 inches, and an average length of approximately 1.932 inches. In other embodiments, sample tubes 675 comprise a diameter from approximately 0.44 inches to approximately 0.48 inches, and a length from approximately 1.8 inches to approximately 1.95 inches. The base floor of cylinder 635 further comprises a hole having a diameter of approximately 1 inch that is configured to receive a polymer vent 680. Polymer vent 680 generally comprises a weatherable polymer material and comprises a central cylindrical passageway 685 having a diameter of approximately 0.625 inches.

Figure 7:
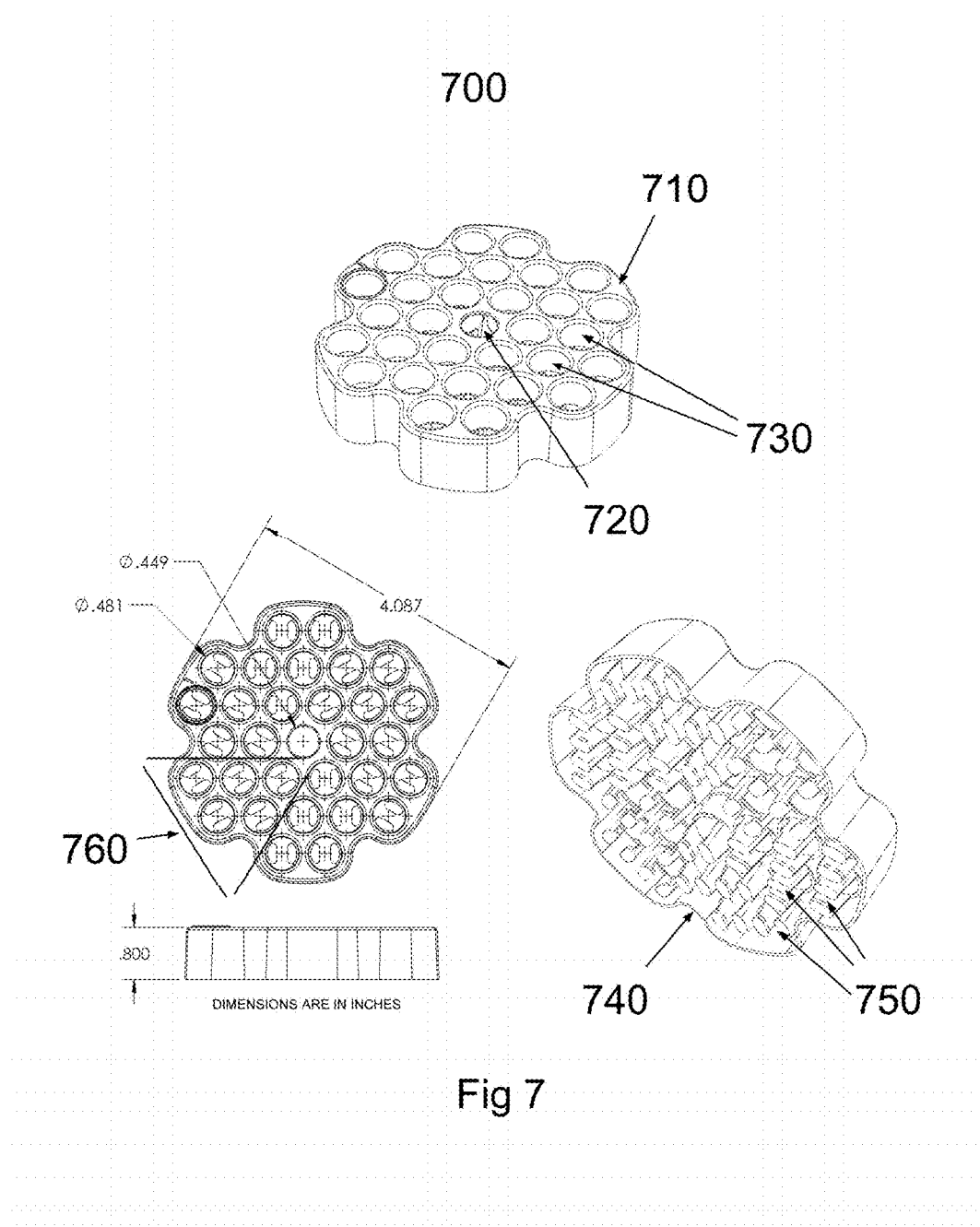
FIG. 7 is a multi-perspective graphic representation of the sample vial rack of the freezing apparatus shown in FIGS. 5 and 6.

Referring now to FIG. 7, a multi-perspective view 700 of the removable sample tube rack 710 is shown. Some embodiments of the present invention comprise a removable sample rack 710 having a radial array of 30 sample bays 730, each bay having an opening comprising a diameter of approximately 0.481 inches. Removable sample rack 710 further comprises a central vent hole 720 having a diameter of approximately 0.449 inches. Central vent hole 720 is provided for the purpose of directing gas flow through removable sample rack 710 during a freezing process.

In some embodiments, removable sample rack 710 further comprises two or more side contours to facilitate handling of the rack. For example, in some embodiments removable sample rack 710 comprises six lobes positioned in a radial array around the outer perimeter of the rack. Each lobe of removable sample rack 710 comprises a repeating unit of 5 sample bays 760 that are arranged at rotational intervals of approximately 60 degrees around central vent hole 720. In some embodiments, removable sample rack comprises a maximum outer dimension of approximately 4.087 inches, and a maximum height of approximately 0.800 inches.

In some embodiments, an outer skirt of removable sample rack 710 terminates in a planar lower edge 740 which is configured to form a gas barrier seal when rack 710 is seated on cylindrical interior shelf 645, as described in FIG. 6. Each sample bay 730 comprises a lower pair of conically tapered grip extensions 750, which terminate to form a bottom foot upon which a bottom surface of the sample vial rests. Upon insertion of a sample vial into sample bay 730, the tapered grip extensions 750 are displaced outwardly thus providing spring tension on the outer wall surface of the vial to retain and secure the vial within the sample bay 730 in an upright, centered position. Spaces or gaps between the outer wall surface of the sample vial, the sample bay 730 and the tapered grip extensions 750 allow for gas flow between the sample vial rack and the sample vial.

In some embodiments, each lobe of removable sample rack 760 comprises five sample bays 730, each sample bay 730 having a pair of tapered grip extensions 750. The orientation of the five sets of tapered grip extensions 750 for each lobe is identical. In some embodiments, six lobes are positioned in a radial array centered on a central vent hole 720. As such, the orientation for the tapered grip extensions 750 for each lobe is in approximate radial alignment with central vent hole 720. In other words, the orientation of the tapered grip extensions 750 for a first lobe is different that the orientation of the tapered grip extensions 750 for an adjacent lobe. This configuration symmetrically distributes the distorting forces from the expanded or outwardly biased tapered grip extension for each lobe, thereby insuring a planar orientation or field of the planar lower edge 740 of removable sample rack 710.

The invention claimed is:

1. A device for freezing two or more samples stored within vials, said device comprising:
   a base having a top end, a bottom end, and a lower chamber extending therebetween and having a first interior volume, the top end having an opening and the bottom end having an inlet port;
   a cover having a top end, a bottom end, and an upper chamber extending therebetween and having a second interior volume, the top end of the cover having an outlet port and the bottom end of the cover having an opening, the bottom end of the cover being configured to interconnect with the top end of the base;
   a sample rack disposed between the base and the cover and configured to receive the vials, wherein the sample rack divides the lower chamber from the upper chamber when the cover is interconnected with the base;
   an interior environment comprising the first and second interior volumes when the cover is interconnected with the base, the interior environment having an initial interior temperature; and
   a gas density gradient within the interior environment from the inlet port to the outlet port when the device is placed in an exterior environment having an environment gas comprising an ambient temperature that is less than the initial interior temperature, wherein heat is removed from the initial interior temperature in part by passive gas diffusion promoted by the gas density gradient.

2. The device of claim 1, wherein the heat is removed via the outlet port as the environment gas is introduced to the interior environment via the inlet port.

3. The device of claim 1, wherein the passive gas diffusion provides a uniform freezing rate for the two or more samples.

4. The device of claim 1, further comprising a gas flow pathway through the interior environment.

5. The device of claim 4, wherein a portion of the sample rack blocks a portion of the gas flow pathway.

6. The device of claim 5, wherein the portion of the sample rack is a perimeter surface.

7. The device of claim 5, wherein the portion of the sample rack is an interface surface between at least one of the base and the cover.

8. The device of claim 5, wherein the portion of the sample rack is an interior surface.

9. A method for freezing a specimen, comprising:
   introducing a sample into a sample rack;
   disposing the sample rack into a sample freezing device comprising:
     a base container having a top end, a bottom end, and a lower chamber extending therebetween, the top end having an opening and the bottom end having an inlet port;

a cover having a top end, a bottom end, and an upper chamber extending therebetween, the top end of the cover having an outlet port and the bottom end of the cover having an opening, the bottom end of the cover being configured to interconnect with the top end of the base container, wherein the sample rack is disposed between the base and the cover, the sample rack comprising a top surface and a bottom surface forming an interface with the base container, wherein the sample rack divides the lower chamber from the upper chamber when the cover is interconnected with the base container to provide an assembled sample freezing device having an interior environment comprising a first environment gas having an interior temperature;

placing the assembled sample freezing device into an environment comprising a second environment gas having an ambient temperature that is less than the interior temperature; and introducing the second environment gas into the interior environment via the inlet port, wherein the second environment gas displaces the first environment gas from the interior environment via the outlet port.

10. The method of claim 9, wherein the second environment is an archival storage site.

11. The method of claim 9, wherein the second environment is a freezer.

12. The method of claim 9, further comprising a step for blocking a gas flow through the sample rack where the sample rack forms an interface with the base container.

13. The method of claim 9, further comprising a step for providing a gas flow through the sample rack at one or more positions proximate to the sample.

14. The method of claim 9, wherein at least one of the base container and the cover comprise a thermo-insulating material.

15. The method of claim 14, wherein the thermo-insulating material is selected from the group consisting of polyethylene, polystyrene, polyurethane foam.

16. The method of claim 9, wherein the sample rack comprises at least one of a thermoconductive material and a thermally inert material.

17. The method of claim 9, wherein the first environment gas comprises a density that is less than a density of the second environment gas.

18. A sample freezing device, comprising:
a base having a top end, a bottom end, and a lower chamber extending therebetween, the top end having an opening and the bottom end having an inlet port;
a cover having a top end, a bottom end, and an upper chamber extending therebetween, the top end of the cover having an outlet port and the bottom end of the cover having an opening, the bottom end of the cover being configured to interconnect with the top end of the base; and
a sample rack disposed between the base and the cover, the sample rack comprising a top surface and a bottom surface, the sample rack forming an interface with at least one of the base and the cover, wherein the sample rack divides the lower chamber from the upper chamber when the cover is interconnected with the base and wherein a gas flow through the sample rack is blocked at the interface.

19. The device of claim 18, wherein the gas flow is further blocked by an interior surface of the sample rack.

20. The device of claim 18, wherein the sample rack further comprises:
a sample bay for receiving a sample vial; and
a gas vent in proximity to the sample bay.

* * * * *